(12) United States Patent
Fisch

(10) Patent No.: US 7,067,557 B2
(45) Date of Patent: Jun. 27, 2006

(54) METHODS OF TREATING ANDROGEN DEFICIENCY IN MEN USING SELECTIVE ANTIESTROGENS

(76) Inventor: Harry Fisch, 30 Springdale Rd., Scarsdale, NY (US) 10583

( * ) Notice: Subject to any disclaimer, the term of this patent is extended or adjusted under 35 U.S.C. 154(b) by 0 days.

(21) Appl. No.: 10/081,098

(22) Filed: Feb. 21, 2002

(65) Prior Publication Data

US 2002/0120012 A1 Aug. 29, 2002

Related U.S. Application Data

(63) Continuation-in-part of application No. 09/980,652, filed on Oct. 26, 2001, now Pat. No. 6,391,920, which is a continuation of application No. PCT/US01/15900, filed on May 15, 2001.

(60) Provisional application No. 60/207,496, filed on May 26, 2000.

(51) Int. Cl.
*A61K 31/135* (2006.01)

(52) U.S. Cl. ................................. 514/648; 514/651
(58) Field of Classification Search .......... 514/648, 514/651
See application file for complete search history.

(56) References Cited

U.S. PATENT DOCUMENTS

| | | | |
|---|---|---|---|
| 5,434,177 A * | 7/1995 | Riekkinen et al. | 514/399 |
| 5,728,688 A | 3/1998 | Labrie | 514/178 |
| 5,861,389 A | 1/1999 | Radlmaier et al. | 514/177 |
| 5,866,584 A * | 2/1999 | Cincotta et al. | 514/288 |
| 6,391,920 B1 * | 5/2002 | Fisch | 514/648 |

OTHER PUBLICATIONS

Basaria, et al. Risks Versus Benefits of Testosterone Therapy in Elderly Men, Drugs & Aging, 1999, Aug.; 15(7); 131–142.*

Lund, et al. "Testosterone and Andropause: The Feasibility of Testosterone Replacement Therapy in Elderly Men." Pharmacotherapy, vol. 19, No. 8, 1999; 951–956.*

The Merck Manual, 14th ed., published 1982 by Merck Sharpe & Dohme Research Laboratories, pp. 916–921.*

* cited by examiner

*Primary Examiner*—Raymond Henley, III
(74) *Attorney, Agent, or Firm*—Ira J. Schaefer, Esq.

(57) ABSTRACT

The administration of antiestrogens to men suffering a relative androgen deficiency stimulates the body's production of testosterone leading to a correction of the deficiency. For example, male menopause, loss of cognitive function, insulin resistance, type 2 diabetes, obesity, excessive weight, Alzheimer's disease, and combinations thereof, can all be characterized by significant decreases in serum levels of bioavailable androgens. Administration of antiestrogens to men restores optimum serum levels of bioavailable androgens, and, thus, serves as a treatment for these disorders and relative androgen deficiency in general.

11 Claims, No Drawings

METHODS OF TREATING ANDROGEN DEFICIENCY IN MEN USING SELECTIVE ANTIESTROGENS

This application is a continuation-in-part application of application Ser. No. 09/980,652 filed Oct. 26, 2001 now U.S. Pat. No. 6,391,920 which claims the priority of PCT/US01/15900 filed May 15, 2001 and which claims priority from application Ser. No. 60/207,496 filed May 26, 2000.

BACKGROUND OF THE INVENTION

The invention relates to the new use of antiestrogens for the production of a pharmaceutical agent for treating a relative androgen deficiency in men.

In men, increasing age leads to a reduction of testicular androgen production and androgen concentration in the organism. In contrast to the situation in women, in whom estrogen production drops to castration values within a comparatively short period, this takes decades in men and involves a gradual drop. The total concentration of testosterone in the serum in the older age group is significantly reduced compared to the values in young men. Because of the increase in steroid hormone-binding globulin (SHBG) that coincides with the aging process, moreover, the proportion of free, unbound, and thus biologically active testosterone drops. In addition, the serum levels of estrogens, although they are produced from androgens by direct conversion, do not drop in the same way as a function of age. As a result, the hormonal environment is significantly altered.

In men, the hormonal environment of the sexual steroids is characterized by a significant preponderance of androgens over estrogens. While the circulating main component of androgens, testosterone, is detected in the serum in units in the range of nmol/l, the estrogen antagonist, estradiol, can be measured only in the range of pmol/l. This considerable preponderance of androgen can be detected basically in the entire late puberty period of life, but there is a clearly different intensity of this androgen dominance as a function of age. With increasing age and particularly so in those over the age of 60, there is a less pronounced emphasis of the androgen preponderance.

In older men there are relative decreases in the preponderance of testosterone by 30–50% compared to the previous values found in young men.

The relative testosterone deficiency per se can be regarded as responsible for a number of age-related disorders. Reduction of muscle mass accompanied by limitation of body performance capacity, reduction of bone density and in individual cases even osteoporosis, an increase in prostate size referred to as benign prostatic hyperplasia, reduction of libido and potency, and psycho-vegetative disorders such as depression and a decline in cognitive functions, which are disorders that are often generically referred to as Male Menopause and are caused by relative androgen deficiency in men. Libido is the desire to obtain an erection, while potency is the ability to have that erection.

It is known that in younger men, testosterone values are also effectively increased by daily treatment with antiestrogens to treat male infertility. Treatment of Male Infertility, Springer-Verlag Berlin, Heidelberg, New York 1982; Fuse, H. et al., Archives of Andrology 31 (1993) 139–145); Nonsurgical Treatment of Male Infertility, Jarow, J., Infertility in the Male, pp. 410–422. However, it has been thought that antiestrogens do not seem well suited for treatment of a relative androgen deficiency in men. Thus, for example, U.S. Pat. No. 5,861,389 proposes the use of at least one aromatase inhibitor for the production of a pharmaceutical agent for treating a relative androgen deficiency in men.

With regard to changes in cognitive function in aging males, there is a relationship between declining levels of testosterone and Alzheimer's disease. Loss of testosterone with aging can result in mental status changes such as loss of cognitive function and can worsen symptoms of Alzheimer's disease. "Testosterone prevents the heat shock-induced overactivation of glycogen synthase kinase-3beta but not of cyclin-dependent kinase 5 and c-Jun NH2-terminal kinase and concomitantly abolishes hyperphosphorylation of tau: Implications for Alzheimer's disease," S. Papasozomenos and A. Shanava, Proc Natl Acad Sci U S A. 2002 Jan. 22. "Testosterone attenuates beta-amyloid toxicity in cultured hippocampal neurons," C. Pike, Brain Res. 2001 Nov. 16; 919(1):160–5. "Testosterone reduces neuronal secretion of Alzheimer's beta-amyloid peptides," Gouras et al, Proc Natl Acad Sci U S A. 2000 Feb. 1 vol. 97 no. 3 pp. 1202–5.

In older men, low testosterone levels is associated with obesity, upper body fat distribution and increased levels of glucose and insulin, and may worsen the symptoms and lead to the development of insulin resistance and type 2 Diabetes (Jee-Young Oh, Elizabeth Barrett-Connor, Nicole M. Wedick and Deborah L. Wingard, Endogenous Sex Hormones And The Development Of Type 2 Diabetes In Older Men And Women: The Rancho Bernardo Study, Diabetes Care, volume 25(1)55–60, January 2002.

SUMMARY OF THE INVENTION

The object of the present invention is to treat a relative androgen deficiency in older men and/or the specific disorders related to male menopause by the use of antiestrogens. The disorders preferably comprise reduction of muscle mass, limitation of body performance capacity, reduction of bone density, reduction of libido, reduction of potency, reduction of benign prostatic hyperplasia, loss of cognitive function, insulin resistance, type 2 Diabetes, obesity, excessive weight, Alzheimer's disease, and combinations thereof.

The use of antiestrogens in treating a relative androgen deficiency in older men results surprisingly in a long-term increase in the androgen level.

By gradually stimulating the body to produce testosterone, the antiestrogens result in an endogenic rebalancing of the testosterone/estrogen ratio in men. As a result, the relative androgen deficiency is compensated for.

For the purposes of this invention, antiestrogens are all those compounds that compete with estrogen for estrogen-receptor-binding sites and may delay replenishment of intracellular estrogen receptors. As antiestrogens, therefore, all such compounds are suitable, such as, for example, tamoxifen or a pharmaceutically acceptable salt thereof and clomiphene or a pharmaceutically acceptable salt thereof, for example:

tamoxifen citrate which is the trans-isomer of a triphenylethylene derivative. The chemical name is (Z)2-[4-(1,2-diphenyl-1-butenyl)phenoxy]-N,N-dimethylethanamine 2-hydroxy-1,2,3-propanetricarboxylate (1:1) and sold under the trademark Novladex; and clomiphene citrate which is 2[p-(2-chloro-1,2-diphenylvinyl)phenoxy]] trieth lamine citrate (1:1). It has the molecular formula of $C_{26}H_{28}ClNO \cdot C_6H_8O_7$ and a molecular weight of 598.09 and is sold under the trademark Clomid.

The list of antiestrogens above is not exhaustive, other compounds that meet the set requirements, are also considered.

A pharmaceutically effective dosage of the antiestrogen is administered in older men for an effective time period, preferably, for 2 years and most preferably continuously. For example, at a daily dose of 5–10 mg once or twice a day, tamoxifen is administered to obtain a target range of mid-normal testosterone levels. A dose of 10–25 mg of clomid daily or every other day and up to 100 mg is administered to obtain the mid-normal levels. Measuring the serum concentration of testosterone and estradiol can thus give early indication of whether the desired hormone balance was achieved and optionally whether dose adjustment can be undertaken.

In general, 5 to 1000 mg, preferably 10 to 100 mg, of antiestrogen clomiphene citrate or tamoxifen citrate or a biologically equieffective amount of another antiestrogen is used daily or every other day to treat a relative androgen deficiency in men.

The antiestrogens can be administered, e.g., orally, parenterally or transdermally by a patch for example.

For the preferred oral administration, suitable means are especially tablets, coated tablets, capsules, pills, suspensions, or solutions that can be produced in a way that is commonly used and familiar to one skilled in the art, with the additives and vehicles that are commonly used for the formulation of antiestrogens that are to be administered orally.

The pharmaceutical agent that is produced according to the invention contains as an active ingredient per dosage unit of the antiestrogen at a daily or every other day dosage of 5 to 100 mg in addition to the commonly used additives, vehicles and/or diluents or other antiestrogens at biologically equieffective dosages.

When antiestrogens are used for treating male menopause, the estrogen concentration is effectively lowered. The easy controllability of the treatment distinguishes treatment with an antiestrogen. For 10 mg tablets, each tablet contains 15.2 mg of tamoxifen citrate which is equivalent to 10 mg of tamoxifen. For 20 mg tablets, each tablet contains 30.4 mg of tamoxifen citrate which is equivalent to 20 mg of tamoxifen. The inactive ingredients are carboxymethylcellulose calcium, magnesium stearate, mannitol and starch.

Clomiphene citrate tablets is a mixture of two geometric isomers [cis(zuclomiphene) and trans (enclomiphene)] containing between 30% and 50% of the cisisomer. A standard commercially available tablet contains 50 mg clomiphene citrate and the following inactive ingredients: corn starch, lactose, magnesium stearate, pregelatinized corn starch, and sucrose. The current tablets are used primarily for treating female infertility. Treatment according to the present invention contemplates a redosing to accommodate the lower dosages specified herein.

It is also contemplated that combinations of antiestrogens can be administered or that combinations of antiestrogens and other testosterone producing drugs can be used.

What is claimed is:

1. A method for treating a decline in cognitive function related to male menopause in men comprising administering a selective antiestrogen.

2. A method for treating Alzheimer's disease related to male menopause in men comprising administering a selective antiestrogen.

3. A method for treating insulin resistance related to male menopause in men comprising administering a selective antiestrogen.

4. A method for treating weight gain related to male menopause comprising administering a selective antiestrogen.

5. A method for treating type 2 diabetes related to male menopause comprising administering a selective antiestrogen.

6. The method according to claim 1, 2, 3, 4, or 5, wherein the selective antiestrogen is tamoxifen.

7. The method according to claim 1, 2, 3, 4, or 5, wherein the selective antiestrogen is tamoxifen citrate.

8. The method according to claim 1, 2, 3, 4, or 5, wherein the selective antiestrogen is clomiphine.

9. The method according to claim 1, 2, 3, 4, or 5, wherein the selective antiestrogen is clomiphine citrate.

10. The method according to claim 9, wherein the clomiphine citrate comprises the cis isomer.

11. The method according to claim 9, wherein the clomiphine citrate comprises the trans isomer.

\* \* \* \* \*